United States Patent [19]

Sykes et al.

[11] 4,339,535

[45] Jul. 13, 1982

[54] PROCESS FOR PREPARING ANTIBIOTIC EM 4940

[75] Inventors: Richard B. Sykes, Rocky Hill; Jerry S. Wells, Ringoes; Wen-Chih Liu, Princeton Junction, all of N.J.

[73] Assignee: E. R. Squibb & Sons, Inc., Princeton, N.J.

[21] Appl. No.: 164,220

[22] Filed: Jun. 30, 1980

Related U.S. Application Data

[62] Division of Ser. No. 70,287, Aug. 27, 1979, Pat. No. 4,249,008.

[51] Int. Cl.³ .............................................. C12P 17/18
[52] U.S. Cl. .................................... 435/119; 435/872
[58] Field of Search ......................................... 435/119

[56] References Cited

U.S. PATENT DOCUMENTS 4,162,940  7/1979  Higashide et al. ................. 435/119

Primary Examiner—Alvin E. Tanenholtz
Attorney, Agent, or Firm—Lawrence S. Levinson; Donald J. Barrack

[57] ABSTRACT

Cultivation of a strain of the microorganism Nocardia sp. 11,340, which has been deposited in the American Type Culture Collection as A.T.C.C. No. 31531, yields a novel antibiotic substance EM 4940, having activity against a range of gram-positive and gram-negative bacteria, yeasts, fungi, acholeplasma, and the protozoan *Trichomonas vaginalis*.

2 Claims, No Drawings

PROCESS FOR PREPARING ANTIBIOTIC EM 4940

This is a division of application Ser. No. 70,287, filed Aug. 27, 1979, now U.S. Pat. No. 4,249,008, issued Feb. 3, 1981.

SUMMARY OF THE INVENTION

Cultivation of a strain of the microorganism Nocardia sp. 11,340, which has been deposited in the American Type Culture Collection as A.T.C.C. No. 31531, yields a novel antibiotic substance EM 4940, having activity against a range of gram-positive and gram-negative bacteria, yeasts, fungi, acholeplasma, and the protozoan *Trichomonas vaginalis.*

The chemical structure of EM 4940, the antibiotic of this invention, has been elucidated through the use of x-ray crystallography and is as follows:

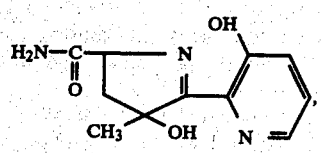

i.e., 3,4-dihydro-4-hydroxy-5-(3-hydroxy-2-pyridinyl)-4-methyl-2H-pyrrole-2-carboxamide. EM4940 is a mixture of two antibiotics, a 2,4-trans isomer and a 2,4-cis isomer, which have been designated EM 4940A and EM 4940B respectively.

DETAILED DESCRIPTION OF THE INVENTION

The Microorganism

The microorganism used for the production of EM 4940 is a strain of Nocardia sp. SC 11, 340. A subculture of the organism can be obtained from the permanent collection of the American Type Culture Collection, Rockville, Maryland. Its accession number in this repository is A.T.C.C. No. 31531. In addition to the specific microorganism described and characterized herein, it should be understood that mutants of the microorganism (e.g., mutants produced through the use of x-rays, ultraviolet radiation or nitrogen mustards) can also be cultivated to produce EM 4940.

Nocardia sp. 11,340, A.T.C.C. No. 31531, can be isolated from a moist soil sample containing the microorganism by first stamping the soil sample on a medium containing:

| | |
|---|---|
| KNO$_3$ | 1 g. |
| K$_2$HPO$_4$ | 0.5 g. |
| MgSO$_4$ . 7H$_2$O | 0.5 g. |
| NaCl | 0.5 g. |
| FeSO$_4$ . 7H$_2$O | 0.01 g. |
| Glucose | 5 g. |
| Agar | 20 g. |
| Distilled water | 1 liter |

The medium is sterilized in an autoclave at 121° C. for 20 minutes. After 14 days incubation at 28° C., colonies of the Nocardia sp. SC 11,340 are isolated from the plated soil. These isolated colonies are then grown on a medium containing:

| | |
|---|---|
| Yeast extract | 1 g. |
| Beef extract | 1 g. |
| NZ Amine A | 2 g. |
| (a casein hydrolysate) | |
| Glucose | 10 g. |
| Agar | 15 g. |
| Distilled water | 1 liter |

The medium is adjusted to pH 7.3 and autoclaved at 121° C. for 30 minutes.

Nocardia sp. Sc 11,340 produces a vegetative mycelium which fragments into rod and coccal forms within 5 days. The cells are nonacid fast and gram-positive.

Colonies growing on a solid medium are smooth to doughly in consistency and are whitish gray in color. On glycerol asparagine agar there are no distinguishing characteristics; on oatmeal tomato paste agar, a soluble purple pigment is produced that permeates throughout the solid medium. No aerial mycelium is formed.

Acid hydrolysates of whole cell walls analyzed by the method of Becker et al., *Applied Microbiology,* 12:421 (1964), indicate the presence of mesodiaminopimelic acid, galactose and arabinose as the major sugar components found. There is some ribbose present but no mudurose. This cell wall analysis represents a Type, IV A pattern (Lechevalier et al, In: The Actionmycetales, H. Pransen (Ed.), VEB Guster Fisher Verlag, pgs. 398–400,402 (1970)) and is diagnostic for the genus Nocardia.

To determine whether acid products are formed from various carbohydrates in the presence of Nocardia sp. SC 11,340, the microorganism is cultured for 10 days on the basal medium of Ayers, Rupp and Johnson, Bull. U.S. Dept. Agri., No. 782 (1919), in the presence of each of the following carbohydrates, with the following results:

| | |
|---|---|
| Basal medium (control) — | Glycerol + |
| Adonitol — | Inositol + |
| Arabinose + | Lactose — |
| Cellobiose — | Maltose + |
| Erythritol — | Mannitol + |
| Glucose + | Mannose — |
| Melezitose — | Xylose — |
| Melibose — | Fructose + |
| Raffinose — | Sucrose — |
| Rhamnose — | Sorbitol — |
| Trehalose — | |

Legend:
+: acids formed
—: acids not formed

Nocardia sp. SC 11,340 decomposes casein and hypoxanthine, but not tyrosine, xanthine and quanine. There is hydrolysis of gelatin, but not starch.

The Antibiotic

The antibiotic EM 4940 can be produced by cultivating Nocardia sp. SC 11,340 A.T.C.C. No. 31531 at, or about, 28° C. under submerged aerobic conditions on an aqueous nutrient medium containing an assimilable carbohydrate and nitrogen source. The fermentation is carried out until substantial antibiotic activity is imparted to the medium, usually about 120 to 144 hours, preferably about 144 hours.

EM 4940 can be separated from the fermentation medium and purified using art-recognized techniques. For example, the broth can be centrifuged to remove the mycelium and then concentrated under reduced pressure. (Alternatively, filtration can be used to remove the mycelium from the broth). Inactive maerial can be precipitated from the concentrate using, for example, methanol, and then discarded. Extraction of the concentrate with ethyl acetate, removes most of the activity. The extract can be concentrated, applied to a chromatography column, e.g., one comprising silicic acid and cellulose, and the antibiotic EM 4940 eluted with chloroform. EM 4940 can be crystallized from acetonitrile. The crystals consist of two forms, (A) platelets and (B) needles. Biologically, the A form is more active than the B form. The two forms are diastereoisomers and cannot usually be distinguished by UV, I.R., mass spectrometry or elemental analysis. One way to distinguish between the two isomers is by proton N.M.R. where the A form has a C—CH$_3$ peak at 1.75 ppm, while the B form has a C—CH$_3$ peak at 1.65 ppm. A mixture of A+B forms has both peaks and from integration of the peaks, one can estimate the percentage of each in the sample. Separation of the two forms can be achieved by fractional crystallization from acetonitrile.

EM 4940 (3,4-dihydro-4-hydroxy-5-(3-hydroxy-2-pyrridinyl)-4-methyl-2H-pyrrole-2-carboxamide) has two assymetric carbon atoms—the carbon atom bearing the carboxamide group and the carbon atom bearing the methyl and hydroxyl groups. Accordingly, 3,4-dihydro-4-hydroxy-5-(3-hydroxy-2-pyridinyl)-4-methyl-2H-pyrrole-2-carboxamide exists in diastereoisomeric forms, or in racemic mixtures thereof. These are all within the scope of this invention.

Detection of EM 4940 is based on a biological diffusion assay utilizing the following medium:

| BBL Seed Agar | 30.5 g. |
| NaCl | 5 g. |
| Distilled Water | 1 liter |

The medium is sterilized at 121° C. for 20 minutes. Agar plates containing sub-inhibitory concentrations of diumycin are seeded with *E. coli* SC 10,888. Under these conditions, EM 4940 is inhibitory to *E. coli* SC 10,888.

The following examples further illustrate this invention.

EXAMPLE 1

A 250 liter batch of Nocardia sp. SC 11,340 A.T.C.C. No. 31531 is fermented in a 100 gallon stainless steel vessel with the media and operating conditions as described below.

Stage 1: Nocardia sp. SC 11,340 is maintained on the following sterilized agar medium (A):

| Oatmeal | 20 g. |
| Tomato paste | 20 g. |
| Agar | 15 g. |
| Tap water to 1 liter | |

The medium is adjusted to pH 7.0 and sterilized at 121° C. for 15 minutes. A loopful of surface growth from an agar slant (Medium A) of Nocardia sp. SC 11,340 A.T.C.C. No. 31531 is suspended in 11 ml of 0.01% dupanol solution and is used as the source of inoculum to inoculate the following sterilized medium (B).

| Yeast extract | 4 g. |

-continued

| Malt extract | 10 g. |
| Dextrose | 4 g. |
| Distilled water to 1 liter | |

The medium is adjusted to pH 7.3 and sterilized at 121° C. for 15 minutes. One thousand five hundred ml of this medium in a 4 liter flask is incubated 72 hours on a rotary shaker at 28° C. (300 rpm, 2 inch stroke).

Stage 2 Inoculum: 1.5 liters from stage 1.

Medium B (28.5 liters, as described above) is adjusted to pH 7.3 and sterilized at 121° C. for 15 minutes. To the sterilized medium is added 1.5 liters from stage 1 and the 30 liters of material is incubated for 72 hours. During incubation, the broth is aerated at the rate of 2.3 cubic feed per minute with agitation at 220 rpm.

Stage 3 Inoculum: 12.5 liters from stage 2

Medium B (237.5 liters, as described above) is prepared as in stage 2 and then combined with 12.5 liters of inoculum from stage 2. The resulting 250 liters of material is incubated for 144 hours. During incubation the broth is agitated at 155 rpm and aerated at the rate of 10 cubic feet per minute.

Removal of the mycelium by centrifugation leaves 185 liters of broth. The clear broth is concentrated under reduced pressure at or below 45° C. to about 3.25 liters. The concentrate is poured slowly into 25 liters of methanol with stirring for 30 minutes, the mixture is centrifuged, and the inactive precipitate is discarded. The supernatant is concentrated under reduced pressure at or below 45° C. to approximately 1.8 liters at which point most of the methanol is removed. The concentrate is then extracted four times with ½ volume ethyl acetate. The ethyl acetate extracts are combined and concentrated under reduced pressure at or below 45° C. to approximately 100 ml, which contains more than 90% of the activity. The ethyl acetate concentrate is loaded onto a silicic acid/cellulose (2:1 by weight) column (43×70 cm), packed in chloroform.

The column is eluted with chloroform. Approximately 3 liters of active material is collected from the column which after concentrating to dryness gives a dry weight of 11–12 g. This material is crystallized from acetonitrile to yield 4.1 g of crystalline EM 4940.

The crystals of EM 4940 consist of two forms, (A) platelets and (B) needles. Biologically, the A form is more active than the B form. The two forms are diastereoisomers and cannot be distinguished by UV, I.R., mass spectrometry or elemental analysis. One way to distinguish between the two isomers, is by proton N.M.R. where the A form has a C—CH$_3$ peak at 1.75 ppm, while the B form has a C—CH$_3$ peak at 1.65 ppm. A mixture of A+B forms has both peaks and from integration of the peaks, one can estimate the percentage of each in the sample. The 4.1 g of EM 4940 obtained above, contains 80% A form and 20% B form. Separation of the two forms is achieved by dissolving the sample in acetonitrile. The B form is more soluble and the A form, therefore, precipitates first; 1.8 g of 97% pure A form is isolated from the sample.

The A form of EM 4940 (platelets) has been determined to be an isomer of 2,4-trans-3,4-dihydro-4-hydroxy-5-(3-hydroxy-2-pyridinyl)-4-methyl-2H-pyrrole-2-carboxamide, and has the following characteristics:

(1) melting point 165°–168° C.

(2) soluble in methanol, ethanol, ethyl acetate, acetone and chloroform Insoluble in hexane and water (3) mass spectrometry—molecular ion=235; empirical formula=$C_{11}H_{13}N_3O_3$ (4) elemental analysis

| Element | Found | Calculated for $C_{11}H_{13}N_3O_3$ |
|---|---|---|
| C | 56.14% | 56.22 |
| H | 5.44% | 5.58 |
| N | 17.66% | 17.88 |
| ash | 0 | |

(5) optical rotation $a_D = +20°$ in methanol

The B form of EM 4940 (needles) has been determined to be an isomer of 2,4-cis-3,4-dihydro-4-hydroxy-5-(3-hydroxy-2-pyridinyl)-4-methyl-2H-pyrrole-2-carboxamide, and has the following characteristics:

(1) melting point 200°–201° C.

(2) mass spectrometry=molecular ion=235; empirical formula—$C_{11}H_{13}N_3O_3$ (3) elemental analysis

| Element | Found | Calculated for $C_{11}H_{13}N_3O_3$ |
|---|---|---|
| C | 56.38 | 56.22 |
| H | 5.60 | 5.58 |
| N | 17.78 | 17.88 |
| ash | 0 | |

EXAMPLE 2

Nocardia sp. SC 11,340 A.T.C.C. No. 31531 is maintained on the following sterilized agar medium (A):

| Oatmeal | 20 g. |
|---|---|
| Tomato paste | 20 g. |
| Agar | 15 g. |
| Tap water to 1 liter | |

The medium is adjusted to pH 7.0 and autoclaved at 121° C. for 15 minutes.

A loopful of surface growth from an agar slant (medium A) of Nocardia sp. SC 11,340 , (ATCC 31531) is used to inoculate each of six 500 ml Erlenmeyer flasks each containing 100 ml of the following sterilized medium (B).

| Yeast extract | 4 g. |
|---|---|
| Malt extract | 10 g. |
| Dextrose | 4 g. |
| Distilled water to 1 liter | |

The medium is adjusted to pH 7.3 before sterilization at 121° C. for 15 minutes. The flasks are then incubated at 28° C. on a rotary shaker (300 rpm; 2 inch stroke) for approximately 72 hours. After the appropriate incubation as described above, 5% (vol/vol) transfers are made from the grown culture flasks to one hundred, 500 ml Erlenmeyer flasks each containing 100 ml of sterilized medium (B) as described above.

After inoculation the flasks are incubated at 28° C. on a rotary shaker (3000 rpm, 2 inch stroke) for approximately 120–144 hours. At this time, the contents of the flasks are pooled and the broth is centrifuged yielding approximately 9 liters of supernatant broth.

The antibiotic is extracted using the procedure described in Example 1.

In addition to the fermentation media utilized in the above examples, the following media are exemplary of others that can be used for the production of EM 4940 and can be substituted for medium B in the above examples:

| Medium C | Grams |
|---|---|
| Yeast Extract | 4 |
| Malt Extract | 10 |
| Dextrose | 25 |
| Distilled H$_2$O to 1 liter | | pH adjusted to 7.3 before sterilization @121° C. for 15 minutes.

| Medium D | Grams |
|---|---|
| Glycerol | 30 |
| Pharmamedia | 20 |
| Yeast Extract | 20 |
| Glucose | 20 |
| Distilled H$_2$O to 1 liter | | pH adjusted to 7.3 before sterilization @121°° C. for 15 minutes.

| Medium E | Grams |
|---|---|
| Yeast Extract | 4 |
| Malt Extract | 10 |
| Glucose | 10 |
| Glycerol | 2 |
| Distilled H$_2$O to 1 liter | | pH adjusted to 7.3 before sterilization @121° C. for 15 minutes.

| Medium F | Grams |
|---|---|
| Glycerol | 10 |
| L-Asparagine | 5 |
| KH$_2$PO$_4$ | 1 |
| Na$_2$HPO$_4$ | 2 |
| Glucose | 50 |
| Mg SO$_4$ . 7H$_2$O | 0.2 |
| Tap H$_2$O to 1 liter | | pH adjusted to 7.3 before sterilization @121° C. for 15 minutes.

| Medium G | Grams |
|---|---|
| (NH$_4$)$_2$SO$_4$ | 2 |
| L-Asparagine | 5 |
| Glucose | 50 |
| Glycerol | 10 |
| KH$_2$PO$_4$ | 7 |
| K$_2$HPO$_4$ | 7 |
| Mg SO$_4$ . 7H$_2$O | 0.2 |
| Distilled H$_2$O to 1 liter | | pH adjusted to 7.3 before sterilization @121° C. for 15 minutes.

BIOLOGICAL TESTING (A) Minimum Inhibitory Concentration (MIC) determination of EM 4940A and EM 4940B against organisms in an aerobic screen.

1. Using BA-2 Agar

The antibiotic is prepared in 0.1 M phosphate buffer pH 7.0 at a concentration of 100 μg/ml. Two fold dilutions are made in Mueller Hinton broth resulting in a range from 1000 μg/ml to 0.5 μg/ml. One ml of each dilution is placed into individual 100×15 mm petri dishes to which 9.0 ml of BA-2 agar are added. The final drug concentration in the agar ranges from 100 μg/ml to 0.05 μg/ml.

All orgainsms are grown in approximately 15–20 ml of antibiotic assay (AA) broth (Difco Bacto antibiotic medium No. 3) by inoculating the broth with a loopful of the organism from a BHI agar slant. The inoculated tubes are incubated at 37° C. for 18–20 hours. Each incubated broth culture is checked for growth level by a visual turbimetric reading against a McFarland No. 5 standard and adjusted accordingly with AA broth (A McFarland No. 5 standard is equivalent to approximately $1 \times 10^9$ CFU/ml CFU is colony forming units). The visual check is made immediately prior to use. The adjusted broth for each organism is then tested at the appropriated inoculum level. For this series of tests in the inoculum level is $10^4$ CFU. The broth cultures were thus diluted 1:100 in AA broth to give $10^7$ CFU/ml. The organisms are then stamped onto the agar plates using a Denley Multi Point Innoculator which delivers 0.001 ml of culture producing an inoculum level of $10^4$ CFU. After stamping, the plates are incubated at 37° C. for 18 hours. The MIC is recorded as the lowest concentration of antibiotic that inhibits the growth of 3 colonies or less.

The results of this procedure are reported in Table I.

TABLE I

| Organism | Number in collection of E. R. Squibb and Sons, Inc. | Minimum Inhibitory Concentration(μg/ml) EM4940A |
|---|---|---|
| Acinetobacter calcoaceticus | 8333 | 50.0 |
| Enterobacter cloacae | 10,459 | >100.0 |
| Escherichia coli | 10,404 | 100.0 |
| Escherichia coli | 10,857 | 50.0 |
| Escherichia coli | 10,896 | 25.0 |
| Klebsiella aerogenes | 10,436 | 100.0 |
| Klebsiella pneumoniae | 11,066 | 50.0 |
| Proteus morganii | 9774 | 50.0 |
| Pseudomonas aeruginosa | 8754 | >100.0 |
| Pseudomonas aeruginosa | 9330 | 50.0 |
| Pseudomonas aeruginosa | 9545 | 25.0 |
| Salmonella typhimurium | 9201 | 50.0 |
| Serratia marcescens | 9782 | 100.0 |
| Serratia marcescens | 1111 | >100.0 |
| Shigella sonnei | 8449 | 50.0 |
| Staphylococcus aureus | 2400 | >100.0 |
| Staphylococcus aureus | 10,165 | 50.0 |
| Staphylococcus aureus | 11,239 | >100.0 |
| Streptococcus faecalis | 9011 | >100.0 |

Additional tests were run using the above methodology and the results of these tests are reported in Table II.

TABLE II

| Organism | Number in collection of E. R. Squibb and Sons, Inc. | Minimum Inhibitory Concentration(μg/ml) | |
|---|---|---|---|
| | | EM4940A | EM4940B |
| Staphylococcus aureus | 2400 | >200 | >200 |
| Staphylococcus aureus | 10,165 | 100 | 100 |
| Staphylococcus aureus | 11,239 | 50 | 100 |
| Staphylococcus aureus | 2661 | >200 | >200 |
| Streptococcus faecalis | 9011 | >200 | >200 |
| Escherichia coli | 10,404 | 50 | 50 |
| Escherichia coli | 10,857 | 50 | 50 |
| Salmonella typhimurium | 9201 | 50 | 50 |
| Klebsiella aerogenes | 10,436 | 50 | 50 |
| K. pneumoniae | 11,066 | 50 | 50 |
| Proteus rettgeri | 8217 | 50 | 50 |
| P. morganii | 9774 | 100 | 100 |
| Serratia marcescens | 9782 | 50 | 50 |
| Serratia marcescens | 11,111 | 100 | 100 |
| Pseudomonas aeruginosa | 9545 | 12.5 | 12.5 |
| Pseudomonas aeruginosa | 8754 | 100 | 100 |
| Pseudomonas aeruginosa | 9330 | >200 | >200 |
| Acinetobacter calcoaceticus | 8333 | 100 | 100 |
| Enterobacter cloacae | 10,459 | 50 | 100 |
| Shigella sonnei | 8449 | 50 | 50 |

(A) Using H-59 Synthetic Agar

The method is as described above except that H-59 agar is substituted for BA-2 agar.

The results of this procedure are described in Table III.

TABLE III

| Organism | Number in collection of E. R. Squibb and Sons, Inc. | Minimum Inhibitory Concentration(μg/ml) EM4940A |
|---|---|---|
| Acinetobacter calcoaceticus | 8333 | 25.0 |
| Enterobacter cloacae | 10,459 | 100.0 |
| Escherichia coli | 10,404 | 50.0 |
| Escherichia coli | 10,857 | 25.0 |
| Klebsiella aerogenes | 10,436 | 50.0 |
| Klebsiella penumoniae | 11,066 | 50.8 |
| Pseudomonas aeruginosa | 8754 | >100.0 |
| Pseudomonas | | |

TABLE III-continued

| Organism | Number in collection of E. R. Squibb and Sons, Inc. | Minimum Inhibitory Concentration(μg/ml) EM4940A |
|---|---|---|
| aeruginosa | 9330 | 50.0 |
| Pesudomonas aeruginosa | 9545 | 25.0 |
| Salmonella typhimurium | 9201 | 50.0 |
| Serratia marcescens | 9782 | 100.0 |
| Serratia marcescens | 11,111 | 100.0 |
| Shigella sonnei | 8449 | 50.0 |
| Streptococcus faecalis | 9011 | >100.0 |

(B) Minimum Inhibitory Concentration (MIC) determination of EM4940A against organisms in an anaerobic screen.

The antibiotic is prepared as described above for the aerobic screen.

All organisms are maintained in a tube of chopped meat broth with glucose supplied by Scott Laboratories in Rhode Island. Two days prior to running the test 0.1 ml of the maintained culture is transferred to a fresh tube of chopped meat broth, and the tube is incubated at 37° C. for 48 hours. After 48 hours incubation each culture is assumed to have grown to $1 \times 10^8$ CFU/ml.

The organisms are stamped onto antibiotic containing agar plates (Mueller Hinton Agar BBL+5% whole sheep blood +0.2% lysed sheep blood) to give an inoculum level of $10^5$ CFU.

After stamping, the plates are placed in an anaerobic gas pack system (BBL) and incubated at 37° C. for 18 hours. The MIC is recorded as the lowest concentration of antibiotic that inhibits the growth of 3 colonies or less.

The results of this procedure are reported in Table IV.

TABLE IV

| Organism | Number in collection of E. R. Squibb and Sons, Inc. | Minimum Inhibitory Concentration(μg/ml) EM4940A |
|---|---|---|
| Bacteroides fragilis | 9005 | 50.00 |
| Bacteroides fragilis | 9844 | 12.50 |
| Bacteroides fragilis | 10,277 | 50.00 |
| Bacteroides fragilis | 10,278 | 50.00 |
| Bacteroides fragilis | 10,279 | 50.00 |
| Bacteroides fragilis | 10,281 | 50.00 |
| Bacteroides fragilis | 11,085 | 100.00 |
| Bacteroides fragilis | 11,086 | 50.00 |
| Bifidobacterium dentium | 11,260 | >100.00 |
| Clostridium histolyticum | 8572 | 12.50 |
| Clostridium perfringens | 11,256 | 50.00 |
| Clostridium septicum | 1780 | 12.50 |
| Clostridium sporogenes | 2372 | 12.50 |
| Eubacterium lentum | 11,261 | 12.50 |
| Fusobacterium necrophorum | 11,338 | 12.50 |
| Hemophilus vaginalis | 8568 | 100.00 |
| Hemophilus vaginalis | 9640 | 100.00 |
| Peptococcus variabilis | 11,264 | 50.00 |
| Peptostreptococcus anaerobius | 11,263 | 50.00 |
| Propionibacterium acnes | 4020 | 50.00 |

(C) Minimum Inhibitory Concentration determination of EM4940A against Candida albicans.

The day previous to running the test, an overnight broth culture of Candida albicans in both F4 broth and yeast nitrogen broth (YNB) is prepared. The overnight broth culture contains approximately $1.0 \times 10^7$ CFU/ml. Both broth cultures are diluted $10^{-3}$ in the respective broths; the antibiotic is prepared at a concentration of 2 mg/ml in 0.1 M phosphate buffer pH 7.0. A 1:8 dilute is of Solution A yields a 1:64 dilution (Solution B).

The test compounds are distributed in $13 \times 100$ mm sterile test tubes procedure, using Kahn pipettes (0.2 ml) according to the following schedule:

| Tube | Addition | Concentration |
|---|---|---|
| 1 | 0.2 ml Stock Solution | 100 μg/ml |
| 2 | 0.1 ml Stock Solution | 50 μg/ml |
| 3 | 0.05 ml Stock Solution | 25 μg/ml |
| 4 | 0.2 ml Solution A (1:8 of stock) | 12.5 μg/ml |
| 5 | 0.0 ml Solution A (1:8 of stock) | 6.3 μg/ml |
| 6 | 0.05 ml Solution A (1:8 of stock) | 3.1 μg/ml |
| 7 | 0.2 ml Solution B (1:64 of stock) | 1.6 μg/ml |
| 8 | 0.1 ml Solution B (1:64 of stock) | 0.8 μg/ml |
| 9 | 0.05 ml Solution B (1:64 of stock) | 0.4 μg/ml |
| 10 | Positive Growth Control (no compound) | — |

To each of the above tubes add 4.0 ml of the $10^{-3}$ dilution of the broth culture to give a final inoculum of $10^4$ CFU/ml.

The tubes are incubated at 37° C. for 18 hours. After this time the results are recorded as: + growth comparable to growth in the control tube; ± growth less than contol tube; − no visible growth.

The MIC is the least concentration of antibiotic giving a negative growth tube. The results of the procedure are reported in Table V.

TABLE V

| Organism | Number in collection of E. R. Squibb and Sons, Inc. | Minimum Inhibitory Concentration(μg/ml) Medium: F4 | Medium: Yeast Nitrogen Base + Glucose |
|---|---|---|---|
| Candida albicans | 5314 | >100 | >100 |

(D) Minimum Inhibitory Concentration determination of EM4940A against dermatophytes.

A 1 mg/ml solution of antibiotic is prepared in 0.1 M phosphate buffer pH 7.0. Two-fold dilutions are made in the broth resulting in a range of antibiotic concentrations from 1000 µg/ml–0.5 µg/ml.

All organisms are grown from shock on F-4 agar slants. Each slant is washed with 10 ml of 0.1 H phosphate buffer pH 7.0. The spore suspension is transferred to a sterile ×4 Morton cap tube and the suspension homogenized.

The prepared agar plates are surface inoculated with 0.2 ml of the appropriate spore suspension. The organism is then streaked across the agar surface using a sterile swab. The inoculated plates are incubated at 26° C. for 48 hours.

The MiC is the highest dilution of each compound series showing no growth. The results of the procedure are reported in Table VI.

TABLE VI

| Organism | Number in collection of E. R. Squibb and Sons, Inc. | Minimum Inhibitory Concentration(µg/ml) EM4940A |
|---|---|---|
| T. mentagrophytes | 2637 | >100 |
| E. floccosum | 9185 | >100 |
| T. rubrum | 9199 | 50 |
| M. canis | 9237 | 100 |

(E) Minimum Inhibitory Concentration determination of EM4940A against *Trichomonas vaginalis*.

Compound preparation is carried out as described under (C). To each series of dilutions, 4 ml of a 1:100 dilution of *T. vaginalis* (grown in modified Diamond's Medium pH 6.0 + 10% rabbit serum) is made from a 40 hour culture.

The tubes are incubated anaerobically at 37° C. for 40 hours and the MIC's determined. The results of the procedure are reported in Table VII.

TABLE VII

| Organism | Number in collection of E. R. Squibb and Sons, Inc. | Minimum Inhibitory Concentration(µg/ml) EM4940A |
|---|---|---|
| Trichomonas vaginalis | 8560 | 12.5 |

(F) Minimum Inhibitory Concentration determination of EM4940A against mycoplasmas.

The antibiotic (1 mg) is dissolved in 200 microliters of dimethylsulfoxide (DMSO). Doubling dilutions are carried out in DMSO over twelve levels to give concentrations ranging from 500–2.49 µg/ml. To two sets of microtitration plates, 5 microliter aliquots of each concentration are transferred in triplicate. Each well of a triplicate set of dilutions is inoculated with 250 microliters of inocultated Channocks broth (10% of 48 hour culture of either *M. mycoides* or *A. laidlawii*). Plates are sealed and examined after 48 hours at 37° C.—for phenol red color change red to yellow and the MIC recorded as the lowest concentration in which no color change occurs.

The results of the procedure are reported in Table VIII.

TABLE VIII

| Organism | MIC (µg/ml) of EM4940A |
|---|---|
| Mycoplasma mycoides | >100 |
| Acholeplasma laidlawii | 100 |

As shown by the above experiments the antibiotics of this invention have activity against a range of gram-positive and gram-negative bacteria, yeasts, fungi, acholeplasma, and the protozoan *Tichomonas vaginalis*. The antibiotics can, therefore, be used as (1) an environmental disinfectant, (e.g., as a spray or dust in a conventional carrier) and (2) an agent to combat infections due to the above-enumerated bacteria, yeasts, fungi, acholesplasma and *Trichomonas vaginalis* in various mammalian species (e.g., topically, orally or parenterally using pharmaceutically acceptable carriers, excipients, etc.).

What is claimed is:

1. A process for the preparation of the compound 3,4-dihydro-4-hydroxy-5-(3-hydroxy-2-pyridinyl)-4-methyl-2H-pyrrole-2-carboxamide which comprises cultivating Nocardia sp. 11,340 A.T.C.C. No. 31531 in an aqueous nutrient medium comprising an assimilable carbohydrate and an assimilable nitrogen source under submerged aerobic conditions until substantial antibiotic activity is imparted to the medium.

2. A process in accordance with claim 1 wherein the microorganism is cultivated at about 28° C.

* * * * *